US011375986B1

(12) United States Patent
Yunis et al.

(10) Patent No.: US 11,375,986 B1
(45) Date of Patent: Jul. 5, 2022

(54) DEVICE AND METHOD FOR STOOL SAMPLE COLLECTION

(71) Applicant: The University of Chicago, Chicago, IL (US)

(72) Inventors: Catherine Yunis, Chicago, IL (US); David Kim, Glenview, IL (US)

(73) Assignees: THE UNIVERSITY OF CHICAGO, Chicago, IL (US); BIOMESENSE, INC., Chicago, IL (US)

( * ) Notice: Subject to any disclaimer, the term of this patent is extended or adjusted under 35 U.S.C. 154(b) by 365 days.

(21) Appl. No.: 16/524,336

(22) Filed: Jul. 29, 2019

Related U.S. Application Data

(60) Provisional application No. 62/711,063, filed on Jul. 27, 2018.

(51) Int. Cl.
*A61B 10/00* (2006.01)
*G01N 1/28* (2006.01)
*G01N 1/10* (2006.01)

(52) U.S. Cl.
CPC ........... *A61B 10/0038* (2013.01); *G01N 1/28* (2013.01); *G01N 2001/1031* (2013.01)

(58) Field of Classification Search
CPC ........ A61B 10/0038; G01N 1/02; G01N 1/10; G01N 2001/1031; G01N 2001/1043; G01N 1/14; G01N 1/22; G01N 2001/2223; G01N 2001/2229; G01N 1/2247; G01N 1/2273
See application file for complete search history.

(56) References Cited

U.S. PATENT DOCUMENTS

| | | | |
|---|---|---|---|
| 2,670,234 A * | 2/1954 | Roop | A47G 21/10 294/99.2 |
| 3,540,433 A | 11/1970 | Brockman | |
| 3,588,921 A | 6/1971 | Nagel | |
| 3,625,654 A * | 12/1971 | Van Duyne | A61B 10/007 600/574 |
| 4,203,169 A * | 5/1980 | Dale | A61B 10/007 4/144.1 |
| 4,259,964 A | 4/1981 | Levine | |
| 4,309,782 A | 1/1982 | Paulin | |
| 4,420,353 A | 12/1983 | Levine | |
| 4,445,235 A * | 5/1984 | Slover | A61B 10/0038 4/144.1 |
| 4,492,124 A | 1/1985 | Fleisher et al. | |

(Continued)

FOREIGN PATENT DOCUMENTS

| CN | 201188074 Y | * | 1/2009 |
|---|---|---|---|
| CN | 202939053 U | * | 5/2013 |

(Continued)

OTHER PUBLICATIONS

Pamela McInnes et al., "Manual of Procedures for Human Microbiome Project Core Microbiome Sampling, Protocol A," HMP Protocol# 07-001, Version No. 12.0, Jul. 29, 2010, pp. 1-116.

*Primary Examiner* — David A. Rogers
(74) *Attorney, Agent, or Firm* — Bell & Manning, LLC.

(57) ABSTRACT

A stool sample collection device includes a catchment unit positioned within a toilet bowl and configured to receive a stool sample. The stool sample collection device also includes a homogenization chamber in which the stool sample is homogenized in a homogenizing solution. The homogenization chamber is configured to receive the stool sample from the catchment unit.

16 Claims, 7 Drawing Sheets

(56) References Cited

U.S. PATENT DOCUMENTS

| | | | | |
|---|---|---|---|---|
| 4,521,520 | A * | 6/1985 | Jacke | G01N 33/726 4/144.2 |
| 4,860,767 | A * | 8/1989 | Maekawa | E03D 11/00 600/573 |
| 4,962,550 | A * | 10/1990 | Ikenaga | A61B 10/007 4/314 |
| 5,730,149 | A * | 3/1998 | Nakayama | G01N 1/12 600/573 |
| 5,882,942 | A * | 3/1999 | Kagaya | A61B 10/0038 436/174 |
| 6,207,113 | B1 * | 3/2001 | Kagaya | A61B 10/0038 422/534 |
| 6,351,857 | B2 | 3/2002 | Slaon, III et al. | |
| 6,555,390 | B2 * | 4/2003 | Chandler | B01L 3/5023 436/518 |
| 6,587,683 | B1 * | 7/2003 | Chow | H04W 76/15 455/417 |
| 6,640,355 | B1 * | 11/2003 | Samide | A61B 10/0038 4/144.2 |
| 6,861,259 | B2 * | 3/2005 | Columbus | G01N 21/03 436/3 |
| 7,011,794 | B2 * | 3/2006 | Kagan | G01N 21/11 356/246 |
| 7,264,776 | B2 * | 9/2007 | Guo | A61B 10/0038 422/411 |
| 7,604,777 | B2 * | 10/2009 | Columbus | G01N 21/03 422/547 |
| 7,815,863 | B2 * | 10/2010 | Kagan | B01L 3/508 422/568 |
| 8,062,901 | B2 * | 11/2011 | Dai | B01L 3/5055 436/165 |
| 8,562,919 | B2 | 10/2013 | Shimada | |
| 9,867,598 | B2 * | 1/2018 | Saito | G01N 1/04 |
| 9,907,541 | B2 * | 3/2018 | Saito | A61B 10/0038 |
| 9,986,978 | B2 * | 6/2018 | Catlin | A61B 10/0038 |
| 10,280,605 | B2 * | 5/2019 | Hall | E03D 11/13 |
| 10,499,886 | B1 * | 12/2019 | Downie | A61B 10/0038 |
| 10,539,570 | B2 * | 1/2020 | Fine | G01N 21/78 |
| 10,729,411 | B2 * | 8/2020 | Wang | G01N 33/483 |
| 11,123,049 | B2 * | 9/2021 | Kramer | E03D 11/00 |
| 2009/0258411 | A1 * | 10/2009 | Petithory | B04B 7/02 435/261 |
| 2010/0121046 | A1 * | 5/2010 | Ahlquist | C12Q 1/6806 536/25.41 |
| 2011/0244461 | A1 * | 10/2011 | Tanigami | C12Q 1/6806 435/6.11 |
| 2011/0270125 | A1 * | 11/2011 | Sonderholm | A61B 10/0038 600/562 |
| 2012/0101481 | A1 * | 4/2012 | Wilson | A61J 1/00 604/540 |
| 2012/0125125 | A1 * | 5/2012 | Li | A61B 10/0038 73/863 |
| 2012/0288956 | A1 * | 11/2012 | Ahlquist | A61B 10/0038 436/174 |
| 2014/0205517 | A1 * | 7/2014 | Ahlquist | B01L 3/00 422/547 |
| 2014/0238154 | A1 * | 8/2014 | Stevens | A61B 10/0038 73/863.52 |
| 2016/0051234 | A1 * | 2/2016 | Gerdes | A61B 10/0038 422/555 |
| 2016/0051445 | A1 * | 2/2016 | Sidorsky | A61J 1/00 435/309.1 |
| 2018/0055489 | A1 * | 3/2018 | Kramer | B01L 3/508 |
| 2018/0085098 | A1 * | 3/2018 | Attar | G01N 33/493 |
| 2018/0271501 | A1 * | 9/2018 | Wang | G01G 19/00 |
| 2019/0010689 | A1 * | 1/2019 | Hall | E03D 11/13 |
| 2019/0059860 | A1 * | 2/2019 | Shahaf | A61B 10/0038 |
| 2019/0062813 | A1 * | 2/2019 | Amin | B01L 3/508 |
| 2020/0225121 | A1 * | 7/2020 | Hall | E03D 11/13 |
| 2020/0271578 | A1 * | 8/2020 | Yamasaki | G01N 21/3577 |
| 2020/0397415 | A1 * | 12/2020 | Yunis | A61B 5/6891 |
| 2021/0187039 | A1 * | 6/2021 | Feldman | B01L 3/5635 |

FOREIGN PATENT DOCUMENTS

| | | | | |
|---|---|---|---|---|
| CN | 102854029 B | * | 11/2015 | ......... A61B 10/0038 |
| CN | 108692785 A | * | 10/2018 | |
| CN | 110461219 A | * | 11/2019 | ......... A61B 10/0038 |
| EP | 727653 A2 | * | 8/1996 | |
| EP | 3040703 A4 | * | 4/2017 | .......... B01L 3/50825 |
| EP | 3610797 A1 | * | 2/2020 | .............. B01L 3/508 |
| JP | 62187253 A | * | 8/1987 | |
| JP | 08285845 A | * | 11/1996 | |
| JP | 2005249553 A | * | 9/2005 | ......... A61B 10/0038 |
| KR | 20130016995 A | * | 2/2013 | |
| WO | WO 2017/051413 | | 3/2017 | |
| WO | WO-2020257542 A1 | * | 12/2020 | ......... A61B 10/0038 |

\* cited by examiner

DEVICE AND METHOD FOR STOOL SAMPLE COLLECTION

CROSS-REFERENCE TO RELATED APPLICATION

The present application claims the priority benefit of U.S. Provisional Patent App. No. 62/711,063 filed on Jul. 27, 2018, the entire disclosure of which is incorporated herein by reference.

BACKGROUND

A stool (or fecal matter) sample includes a significant amount of information regarding the health and status of an individual, and can provide valuable information regarding treatment options for various conditions. For example, a fecal occult blood test can be used to diagnose conditions that cause bleeding in an individual's gastrointestinal system, including various cancers. Also, parasitic diseases (e.g., ascariasis, hookworm, strongyloidiasis, whipworm, etc.) can be diagnosed by detection of worm larvae or eggs in a stool sample. Bacterial diseases, toxins, viruses, lactose intolerance, pancreatitis, etc. can also be identified/diagnosed based on stool sample analysis. With recent advances in testing procedures, deoxyribonucleic acid (DNA) tests can also be performed using a stool sample.

SUMMARY

An illustrative stool sample collection device includes a catchment unit positioned within a toilet bowl and configured to receive a stool sample. The stool sample collection device also includes a homogenization chamber in which the stool sample is homogenized in a homogenizing solution. The homogenization chamber is configured to receive the stool sample from the catchment unit.

An illustrative method for collecting stool samples includes receiving a stool sample on a catchment unit of a stool sample collection device. The method also includes retracting the catchment unit and the stool sample into a homogenization chamber of the stool sample collection device. The method also includes homogenizing the stool sample with a homogenizing solution within the homogenization chamber.

Another illustrative stool sample collection device includes a catchment unit positioned within a toilet bowl and configured to receive a stool sample, a homogenization chamber, and a processor configured to control the catchment unit and the homogenization chamber. The processor is configured to move at least a portion of the catchment unit that includes the stool sample into the homogenization chamber. The processor is also configured to homogenize the stool sample in a homogenizing solution within the homogenization chamber. The processor is further configured to remove the homogenized stool sample from the homogenization chamber Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
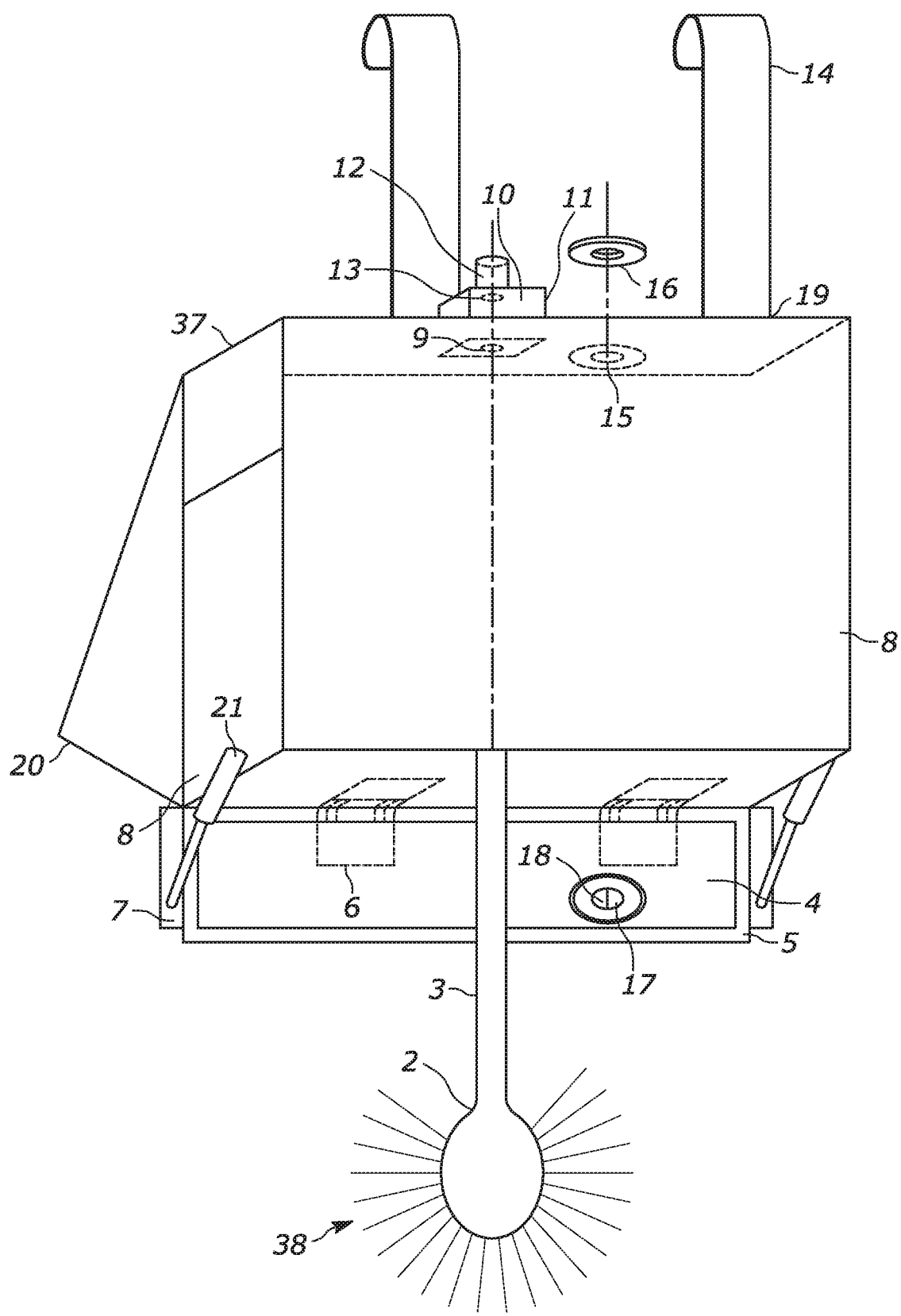
FIG. 1 depicts a first subassembly of a stool collection device in accordance with an illustrative embodiment.

As discussed above, stool samples are currently used for a variety of purposes in the health field. However, despite advances in the understanding of the role of the stool microbiome in human health and therapeutic efficacy, there is a significant gap between the research potential and actual clinical implementation. Except for a few therapeutics and probiotics, the average patient has no way to leverage their stool microbiome for improved outcomes. Of particular note is the lack of stool microbiome use in therapeutic development. Multiple studies have demonstrated the stool microbiome's impact on how humans process various therapeutics and its potential as a novel biomarker, including predicting anti-PD-1 efficacy. Despite these data, microbiome use in drug development is limited, and less than 1% of Phase I, II, and III trials use microbiome testing today. This limited use is due to a number of challenges specific to the stool microbiome.

One challenge is that a human stool microbiome, while compositionally stable over long periods in adults, shows dramatic variability day-to-day in the relative proportions of the membership. These variations can lead to biomarkers being misidentified due to their fluctuating abundance. This variation can also be exacerbated by short-term events, such as illness, diet changes, and travel. Put together, these factors sharply lower the statistical significance of any single snapshot of a stool microbiome as this single look may not accurately reflect the long-term, stable stool microbiome composition.

Another challenge is that a stool microbiome has dynamic and complex responses to any outside intervention, making it challenging to determine causation. For example, before introducing a new therapeutic to a patient, that patient's stool microbiome is in a steady state. When a new drug is taken, it can be influenced by this steady-state stool microbiome, impacting side effects, efficacy, dosing, and more, along the same lines as patient genetics. However, the stool microbiome has one critical distinction from genetics—it is not a fixed variable, but instead can be influenced by both the drug and the patient during the course of the trial, thereby changing over time. This makes controlling potential confounding variables extraordinarily difficult.

The only robust, reliable solution to the above challenges is time-longitudinal sampling of a patient's stool microbiome throughout a trial. In fact, in unpublished preliminary data, the ability to capture the variance of the microbiome within a cohort is resolved if more than 32 daily longitudinal samples are collected. In alternative implementations, a different number of daily longitudinal samples may be used. The use of daily longitudinal samples solves both the variance concern due to the high sample volume and the complexity concern by allowing researchers to isolate variables to daily timescales, ensuring clinical changes are directly associated with the stool microbiome on a given day. Having this data would allow researchers to draw far more robust conclusions from their trials, and therefore accelerate clinical implementation.

Today, however, stool microbiome sampling requires manual stool collection, processing, and data generation, which has several issues, the most prevalent of which is patient reluctance to interact with their own stool as part of a trial. This reluctance results in low patient adherence (commonly <40%) for even single samples, meaning collection of longitudinal microbiome data is very difficult to achieve. Described herein are methods and devices intended to eliminate the challenges of collecting an adequate number of stool samples from patients.

More specifically, described herein are methods and devices for collecting stool samples in a fully automated, minimally invasive way, thereby eliminating adherence concerns. The embodiments described herein achieve this objective through a unique system design that allows stool sample collection with little or no patient interaction. The stool samples are collected without interrupting the patient's normal routine and do not require the patient to directly touch or otherwise manipulate the stool sample during the collection process. The embodiments described herein also ensure that stool samples avoid contamination from the environment during collection, and the system is fully self-cleaning, which prevents cross-contamination between samples. It is envisioned that the described embodiments will result in a total paradigm shift in how stool microbiome research is conducted. The proposed stool collection devices can be immediately incorporated into trials, providing far superior longitudinal data at a fraction of the cost of current methods. The proposed stool collection devices will also supercharge microbiome clinical use as a biomarker and diagnostic, and therefore have an impact on any and all microbiome-related therapeutics, clinical practices, diets, and more, helping to usher in a new avenue of precision medicine. In addition to microbiome-related use, the proposed embodiments may also be used to collect stool samples for any downstream analysis, including but not limited to fecal occult blood tests, cancer screenings, and DNA tests.

FIG. 1 depicts a first subassembly of a stool collection device in accordance with an illustrative embodiment. The stool collection device performs fully automated sample collection, and can be mounted in a patient's home for easy use and access. The stool collection device does not require the patient (or user) to interact directly with the stool sample, which helps remove the reluctance that many patients have in collecting stool samples.

The first subassembly depicted in FIG. 1 is configured to mount to a toilet and includes a homogenization chamber 8 and a catchment unit 38 that retractably extends from the homogenization chamber 8. As depicted in FIG. 1, a door 4 of the homogenization chamber 8 is in an open position and the catchment unit 38 is in an extended position, ready to collect a sample. Upon collection of a stool sample by the catchment unit 38, the catchment unit 38 retracts into the homogenization chamber 8 through a mechanism such as a telescoping arm, a pulley, a gear and rack arm, along a magnetized track, via a linear state, etc., and the door 4 of the homogenization chamber 8 closes such that homogenization of the collected sample can be performed.

In one embodiment, an initial state of the catchment unit 38 can be the extended position shown in FIG. 1, and the catchment unit 38 can remain in that position until a stool sample is deposited thereon. Upon detection of a stool sample, the catchment unit 38 automatically retracts into the homogenization chamber 8 and the door 4 closes such that homogenization, packaging, processing, cleaning, etc. can be performed as described in more detail below. The first subassembly can detect the stool sample and begin retraction of the catchment unit 38 via one or more sensors included in the first subassembly. The one or more sensors can include a motion sensor that detects movement proximate to the catchment unit 38, a mass sensor incorporated into the catchment unit 38, an image sensor that detects the presence of matter on the catchment unit 38, etc. In an alternative embodiment, retraction of the catchment unit 38 can be initiated by a user action, such as pressing of a button on the first subassembly.

In an alternative embodiment, the initial state of the catchment unit 38 can be a retracted position in which the catchment unit 38 is retracted within the homogenization chamber 8. Having the initial state be in a retracted position can help to prevent the catchment unit 38 from being contaminated by other users of the toilet (i.e., users other than the individual whose stool samples are being collected), by urine, by toilet bowl water, by toilet bowl cleaners, etc. In such an embodiment, the catchment unit 38 can be extended in response to a user pressing a button 12 (or activating another control) on the first subassembly. In another embodiment, the catchment unit 38 can automatically extend responsive to the detection of a user via one or more motion sensors, one or more image sensors, etc. In yet another embodiment, the user can use a remote device such as a smart phone, tablet, laptop computer, desktop computer, etc. to remotely activate the device. The smart phone or other computing device can include a dedicated application used to control and interact with the stool collection device.

As depicted in FIG. 1, the catchment unit 38 includes catch fingers 1, a catch base 2, and a catch arm 3. In alternative embodiments, different configurations, components, shapes, etc. may be used for the catchment unit 38. For example, the catchment unit 38 of FIG. 1 has a hand shape. In alternative embodiments, the catchment unit 38 can take the form of a toilet bowl bristle/brush, a foam ball, a funnel, a cup, a net, a mesh similar to a tennis racket, an inward facing bristle circle, a hexagonal plate, a steel brush, a coiled wire, a suction tube, a chain chomp, a disposable basin with a lid and handle, fabric on rollers, a dustpan with an air sweep, a q-tip shaped end with extendable needle arms that retract to pull back the sample into a handle and up to the chamber, a sieve, a 4 leaf clover design (i.e., multiple leaves with a connecting center stem), a spiky roller/hair brush shape, a toothbrush shape, a corkscrew transport tube, a stool platform, a conveyor belt, a mandolin that slices a stool sample for placement into a tube, needles, etc. In an illustrative embodiment, the primary sample collection occurs on the catch fingers 1, which are supported by the catch base 2, which in turn is mounted to the catch arm 3. In such an embodiment, the catch arm 3 and catch base 2 can be flat or have a convex shape to help prevent stool from accumulating thereon. Such an implementation aids with cleaning of the catchment unit once the stool sample has been collected. In an alternative embodiment, the catch base 2 and/or catch arm 3 can have a concave shape intended to aid in stool sample collection. Any number of catch fingers may be used, such as 1, 2, 5, 10, 20, 30, 50, etc. The components of the catchment unit can be made from stainless steel, titanium, plexi-glass, plastic, non-reactive metallic wire, etc.

Upon collection of a stool sample on the catchment unit 38, the catchment unit 38 along with the stool deposited thereon retracts into the homogenization chamber 8 of the first subassembly. In an illustrative embodiment, an intake motor 11 incorporated into the first subassembly is used to retract the catchment unit 38 into the homogenization chamber 8. The catchment unit 38 can retract automatically upon sensing the presence of a stool sample. In one embodiment, the catchment unit 38 retracts a predetermined amount of time after sensing the stool sample (e.g., 1 minute, 5 minutes, etc.) so as not to disturb the user while he/she is still going to the bathroom. The catchment unit 38 can also retract responsive to automatically sensing that the user has left the toilet via motion sensors, image sensors, etc. Alternatively, the catchment unit 38 may retract responsive to the user pressing a button (e.g. the button 12) or sending a remote instruction to the device through a smart phone or other computing device.

As the catchment unit 38 retracts, at least a portion of the catch arm 3 can extend through a hole 9 and a hole 13 in the homogenization chamber 8. The hole 9 and the hole 13 are through holes that allow the catchment unit 38 to move up for retraction and down for deployment. Additionally, as the catchment unit 38 retracts, the door 4 of the homogenization chamber 8 automatically closes to seal the homogenization chamber from the surrounding environment. The door 4 includes a sealing layer 5 to form the seal, which is a liquid tight seal in an illustrative embodiment. The door 4 also includes a flange 7 on each side to which a solenoid 21 is mounted for automatically controlling opening/closing of the door 4. In an alternative embodiment, the solenoids 21 may be mounted directly to an exterior side of the door 4 and the flanges 7 may not be included. In another alternative embodiment, a component other than a solenoid can be used to control movement of the door 4. The door 4 also includes spring-loaded hinges 6 that assist with closing of the door 4 and to help form the watertight seal once the door 4 is closed. In an alternative embodiment, the spring-loaded hinges 6 may not be used. In such an embodiment, one or more regular hinges can be used and the solenoids 21 can be used to maintain pressure on the door 4 to ensure that the seal is watertight. In another embodiment, one or more clamps can be used to secure the door 4 in a closed position. Alternatively, an electronic locking mechanism can also be used to help keep the door 4 shut and watertight.

The door 4 is depicted as a single door across a surface of the homogenization chamber 8. Alternatively, the door could be implemented as a door positioned on a corner of the chamber as opposed to the bottom, as double doors, as a screw plug, as a fitted cover for the entire bottom of the chamber, as a sliding door, as a door with multiple flaps that open/close similar to a flower, etc. The door and other components of the device can be made of any material with high chemical resistance, and can be hydrophobic. Additionally, sealant/caulking can be used throughout the device to ensure that it is water tight.

Once the catchment unit 38 is retracted and the door 4 is shut, the stool sample is homogenized using a homogenizing solution such as water. In alternative embodiments, the homogenizing solution can be a saline solution, a phosphate-buffered saline (PBS) solution, lysogeny broth (LB), water with bacterial nutrients, salt solution, etc. In another embodiment, liquid nitrogen can be used to freeze the stool sample into a solid form. The homogenizing solution is received via an opening 15 in the homogenization chamber 8. A backflow gasket 16 is positioned within the opening 15 to prevent any backflow of the contents of the homogenization chamber 8 into the source of the homogenizing solution. Alternatively, instead of a backflow gasket, the device can use a gate at the opening 15 that shuts when water is no longer needed and is actuated by the controllers or by reversing the flow of water to empty a hose connected to the opening 15.

A homogenization motor 10 is used to actuate the catchment unit 38 within the homogenizing solution such that the stool sample is removed from the catchment unit 38 and mixed with the homogenizing solution. The homogenization motor 10 can actuate the catchment unit 38 through rotation, spinning, back-and-forth movements, by sending a vibration/shock through the catchment unit 38, etc. The actuation of the catchment unit 38 within the homogenizing solution can occur for a predetermined amount of time such as 30 seconds, 1 minute, 2 minutes, 5 minutes, etc. In an alternative embodiment, jets or other actuators can be used to shoot/move pressurized water within the homogenization chamber 8, and the catchment unit 38 can remain stationary during the homogenization process. In another embodiment, rotating cloth rollers can be used to clean the catchment unit 38 similar to a car wash. In another embodiment, the homogenization chamber 8 and/or homogenizing solution can be heated to assist with removal of the stool from the catchment unit 38 and/or a chemical (e.g., salt) can be added to the homogenizing solution to help with removal. Alternatively, the catchment unit can be rubbed/scraped across a surface that removes the sample by friction. Once the sample is homogenized in the homogenizing solution, the homogenization chamber 8 is drained through an opening 17 that includes a grate 18 to strain any portions of non-homogenized stool sample. The opening 17 can include an actuated gasket to open/close the opening as known in the art.

The first subassembly also includes a microcontroller (or processor) 37 to control the homogenization motor 10, the intake motor 11, the solenoids 21, gaskets, and any other electronic or electrically controllable components incorporated into the first assembly, such as an electronic lock to keep the door 4 closed during homogenization. The microcontroller can actuate solenoid control valves in one embodiment to control the flow of liquid through any of the openings in the device. Any type of microcontroller known in the art may be used. In an alternative embodiment, the microcontroller 37 may be housed in a second subassembly of the system, which is described with reference to FIG. 2.

Figure 3:
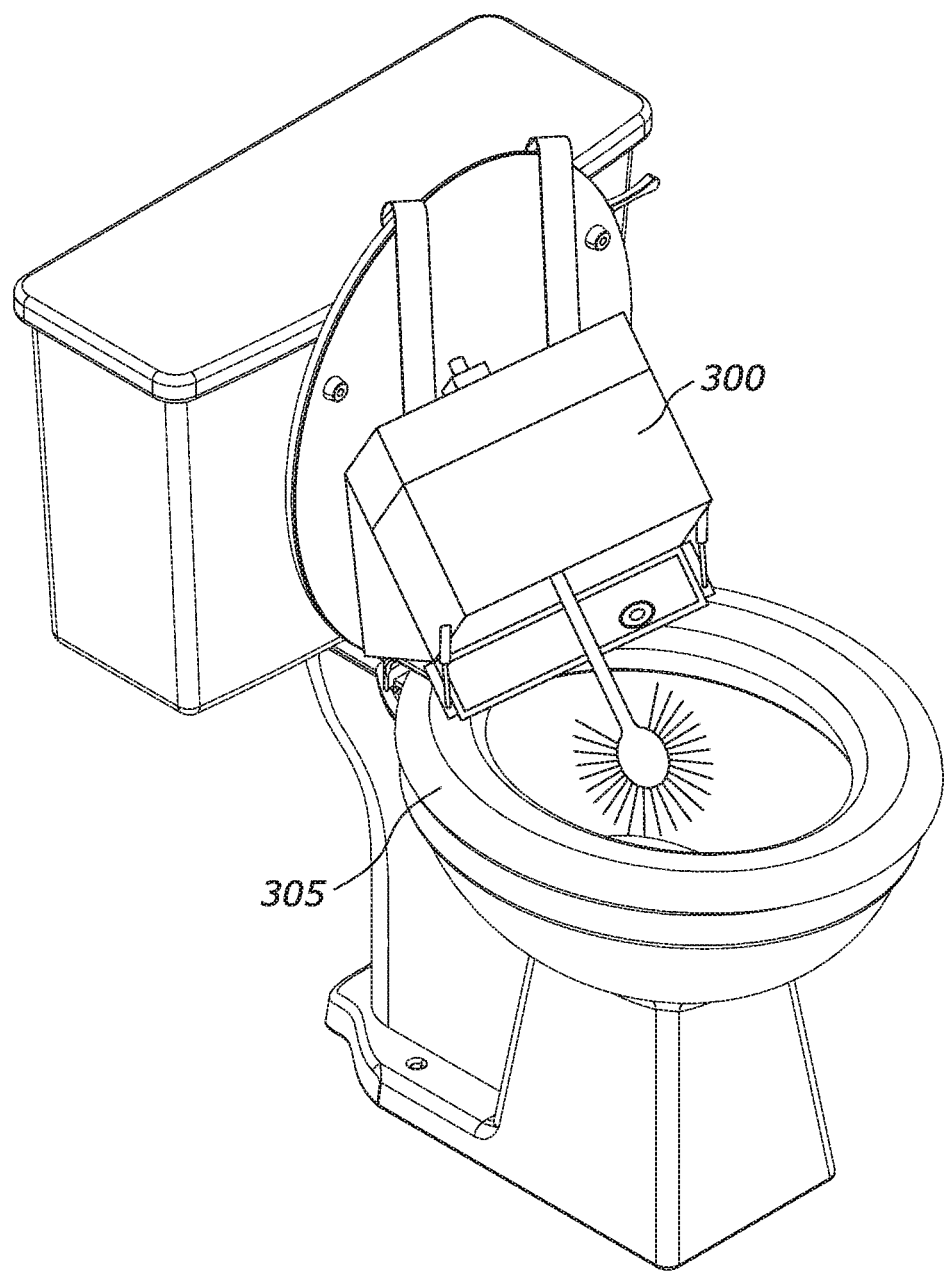
FIG. 3 depicts a first subassembly of a stool collection device mounted to a toilet in accordance with an illustrative embodiment.

In one embodiment, the first subassembly is mounted to a standard toilet in a patient's home using hooks 14, which are mounted to the homogenization chamber 8 through an attachment 19. The attachment 19 can be one or more fasteners, a weld, a solder, a clip, a male/female connection, etc. The hooks 14 can be used to hang the first subassembly from an upright toilet seat lid and/or from a toilet water tank. FIG. 3 depicts a first subassembly 300 of a stool collection device mounted to a toilet 305 in accordance with an illustrative embodiment. In alternative embodiments, the first subassembly may not include hooks and can instead be mounted to the toilet through the toilet seat fasteners used to mount the toilet seat to the toilet bowl, through the fasteners used to mount the toilet bowl to the floor, through double sided tape, with suction cups, with magnets, using caulk/putty, with Velcro®, with one or more straps that wrap around the water chamber of the toilet, with supportive stilts that rest on the toilet seat or floor, with epoxy or other adhesive, etc. The first subassembly can also be mounted to a wall or ceiling adjacent to the toilet such that the first subassembly rests on or adjacent to the toilet. As shown in FIG. 1, the first subassembly also includes a wedge 20 on each side of the homogenization chamber 8 to help ensure that the first assembly is mounted in the proper orientation on the toilet. The wedges 20 can be adjustable to accommodate toilets of different sizes and shapes.

Figure 2:
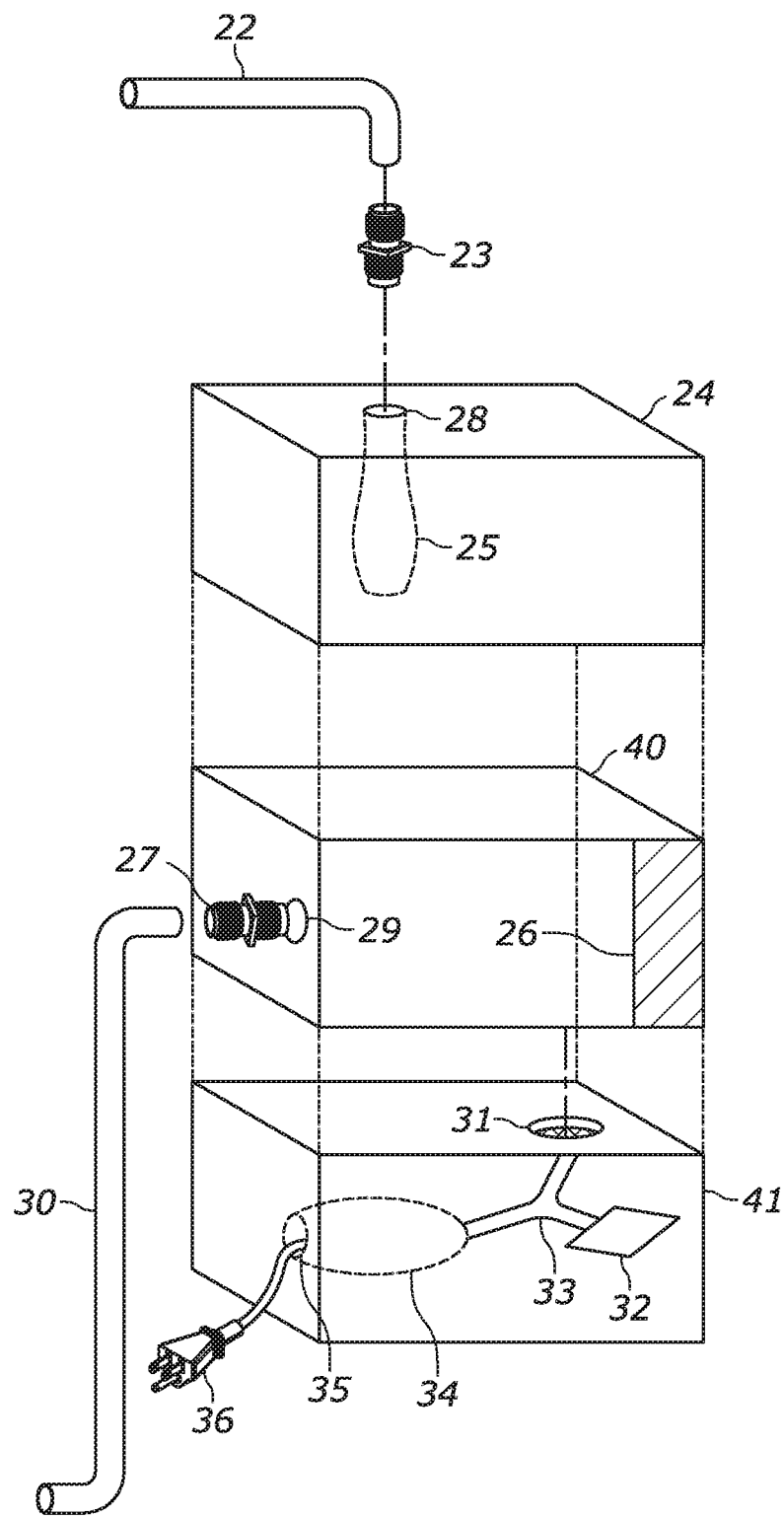
FIG. 2 depicts an exploded view of a second subassembly of a stool collection device in accordance with an illustrative embodiment.
Figure 4:
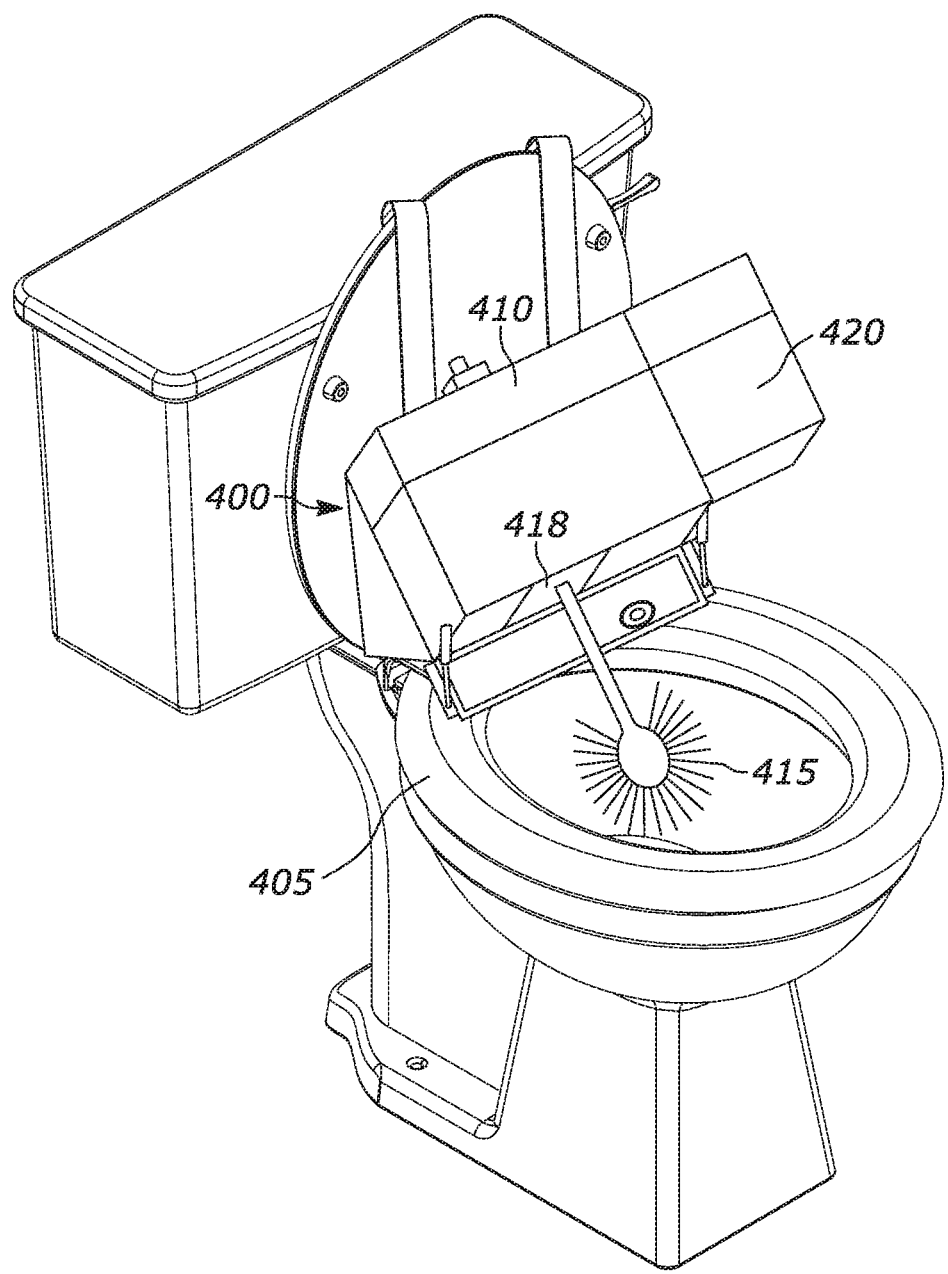
FIG. 4 depicts a stool collection device mounted to a toilet seat in accordance with an illustrative embodiment.

FIG. 2 depicts an exploded view of a second subassembly of a stool collection device in accordance with an illustrative embodiment. The second subassembly is positioned near the toilet and used to receive, process, analyze, and/or package the homogenized stool sample. The second subassembly is also used to clean the entire system, as discussed below. The second subassembly includes a homogenizing solution chamber 24, a sample chamber 40, and a cleaning solution chamber 41. In alternative embodiments, fewer or additional chambers may be included. For example, in one embodiment, the sample chamber 40 may be eliminated and the homogenized sample can be received directly at the cleaning solution chamber 41. In other alternative embodiments, both the first subassembly and the second subassembly can be combined into a single assembly, as shown in FIG. 4, which is described below. A power cord 36 extends through an opening 35 in the cleaning solution chamber 41, and is used to provide power to the first and second subassemblies of the device. Alternatively, the power cord 36 can be positioned elsewhere and/or each of the first and second subassemblies can include a separate power supply.

The homogenizing solution chamber 24 includes a supply of homogenizing solution that is pumped through an opening 28 and into a hose 22 (or tube), which in turn connects to the opening 15 in the homogenization chamber 8 of the first subassembly. A hose fitting 23 is used to secure the hose 22 to the homogenizing solution chamber 24. The homogenizing solution is pumped using a pump 25, which can be a pneumatic pump or any other type of pump known in the art. In an illustrative embodiment, the homogenizing solution chamber 24 can include enough homogenizing solution to last the user an extended amount of time, such as a month, 2 months, etc. In one embodiment, the homogenizing solution chamber 24 can include an access panel/door/opening that allows the user to fill the chamber 24 by pouring in the homogenizing solution or by placing a receptacle that contains the homogenizing solution into the chamber 24. Alternatively, the user can remove the hose 22 and fill the homogenizing solution chamber 24 via the opening 28.

In an alternative embodiment in which the homogenizing solution is water, the homogenizing solution chamber 24 may be eliminated from the second subassembly. In such an embodiment, the hose 22 can run directly from the homogenization chamber 8 to a water supply such as the water supply used to flush the toilet bowl. A y-valve, y-tube, T-valve, etc. can be used to ensure that both the toilet bowl and the homogenization chamber 8 are able to receive water as needed. The water used for homogenization can alternatively be siphoned from the toilet tank. In another alternative embodiment, the homogenizing solution can be stored at the first subassembly described with reference to FIG. 1, stored elsewhere on/in the toilet, or stored elsewhere remote from the toilet.

The sample chamber 40 receives the homogenized sample from the homogenization chamber 8 through a hose (or tube) 30 that is mounted to an opening 29 in the sample chamber 40 using a hose fitting 27. In an illustrative embodiment, the homogenized sample is fed to the sample chamber 40 through gravity. Alternatively, a pump may be used. The sample chamber 40 includes a microcontroller 26 that is used to control any of the pumps and other electronic components of the second subassembly. In alternative embodiments, the microcontroller 26 can be positioned elsewhere within the second subassembly, or in the first subassembly depicted in FIG. 1.

In one embodiment, the sample chamber 40 can be used to prepare the homogenized sample for onsite analysis. For example, the sample chamber 40 may include a heating element that is used to heat the sample as part of a sample analysis process. Alternatively, sample analysis may be performed off-site. In such an embodiment, the device is used to package the homogenized sample so that the user can send it in for analysis. The packaging process can be performed within the cleaning solution chamber 41 as described below. Alternatively, the packaging process may be performed within the sample chamber 40 or in a separate packaging chamber/unit which can be incorporated into the device. In one embodiment, the system can include a refrigeration system used to chill or freeze the collected sample.

The cleaning solution chamber 41 is connected to the sample chamber 40 through an opening 31. The homogenized sample enters the cleaning solution chamber 41 through the opening, which can align with another opening in the bottom of the sample chamber 40. As discussed above, in an alternative embodiment the sample chamber 40 may be excluded and the hose 30 can connect directly to the opening 31 of the cleaning solution chamber 41. The homogenized sample passes through one branch of a T-valve 33 into a receptacle 32 that includes an analysis unit for analyzing the homogenized sample and/or vessels for packaging the homogenized sample. Alternatively, instead of a T-valve, a solenoid gasket may be used. The vessels can be test tubes, plastic containers, etc. In an illustrative embodiment, at least a portion of the homogenized sample is placed into a vessel and the vessel is automatically sealed to prevent contamination of the sample. The vessel can be sealed with a screw on lid, a stopper, or any other technique. The sealed vessel, which is clean and sanitary, can be accessed by the user through a door or other opening in the chamber 41 and taken/sent to a lab for further processing.

In an alternative embodiment, the sample may not be packaged by the device. In such an embodiment, the receptacle 32 of the cleaning solution chamber 41 can be used to house an analysis unit for conducting tests/analysis of the sample on-site. Results of the testing/analysis can be stored in a computer memory of the device and/or transmitted to a remote location through a network using a transceiver of the device. In another embodiment, the device is configured to both analyze the sample on-site and package the sample for additional processing off-site. In such an embodiment, at least a portion of the sample can be analyzed on-site, and that same portion of the sample can be packaged for additional processing. Alternatively, a first portion of the sample can be analyzed on-site and a second portion of the sample can be packaged for additional processing.

At least a portion of the cleaning solution chamber 41 includes a cleaning solution that is used to clean and disinfect all components of the device that contacted the stool sample. The cleaning and disinfection is performed in between sample collections so that one sample does not contaminate a subsequent sample. The cleaning solution can be bleach, hot water, a pressurized water wash, drain cleaner, soap and water, a bleach wash with subsequent water rinse, and/or any other disinfectant known in the art. A pump 34 is used to pump the cleaning solution through the T-valve 33, through the opening 31, through the solution chamber 40, through the hose 30, through the opening 17, and into the homogenization chamber 8 so that the entire device is cleaned and disinfected. The pump 34 can be a primed pump that pumps the cleaning solution through the system, pushing out the residual of the homogenized sample. The cleaning solution can remain in the device chambers for a timed soak to help ensure that complete disinfection occurs. In one embodiment, the cleaning solution and any residual of the homogenized sample is then deposited into the toilet by opening the door 4 of the homogenization chamber 8. Alternatively, the cleaning solution and residual sample can exit through a designated port that is in communication with the toilet bowl or another drain. In one embodiment, the device can be flushed with additional cleaning solution and/or clean homogenizing solution (i.e., from the homogenizing solution chamber 24) after the initial cleaning solution and any residuals of the sample have been removed.

FIG. 4 depicts a stool collection device 400 mounted to a toilet seat 405 in accordance with an illustrative embodiment. In the stool collection device 400 of FIG. 4, both the first subassembly and the second subassembly are combined into a single unit, which is mounted to the toilet seat. Specifically, the stool collection device 400 includes a homogenization chamber 410 with a retractable catchment unit 415 extending therefrom. The retractable catchment unit 415 is controlled by a motor 418 as described herein. The stool collection device 400 also includes a solution chamber 420, which can include the homogenizing solution and/or cleaning solution. In an illustrative embodiment, sample processing and/or packaging can occur within the homogenization chamber 410 or the solution chamber 420 of the stool collection device 400. Alternatively, the stool collection device 400 can include a separate processing/packaging chamber (not shown) in which sample processing and/or packaging occurs as described herein. In such an embodiment, the separate processing/packaging chamber can be connected to the main assembly via one or more hoses, tubes, etc. The stool collection device 400 can include components similar to and can function similar to the stool collection devices described with reference to FIGS. 1 and 2.

Figure 5:
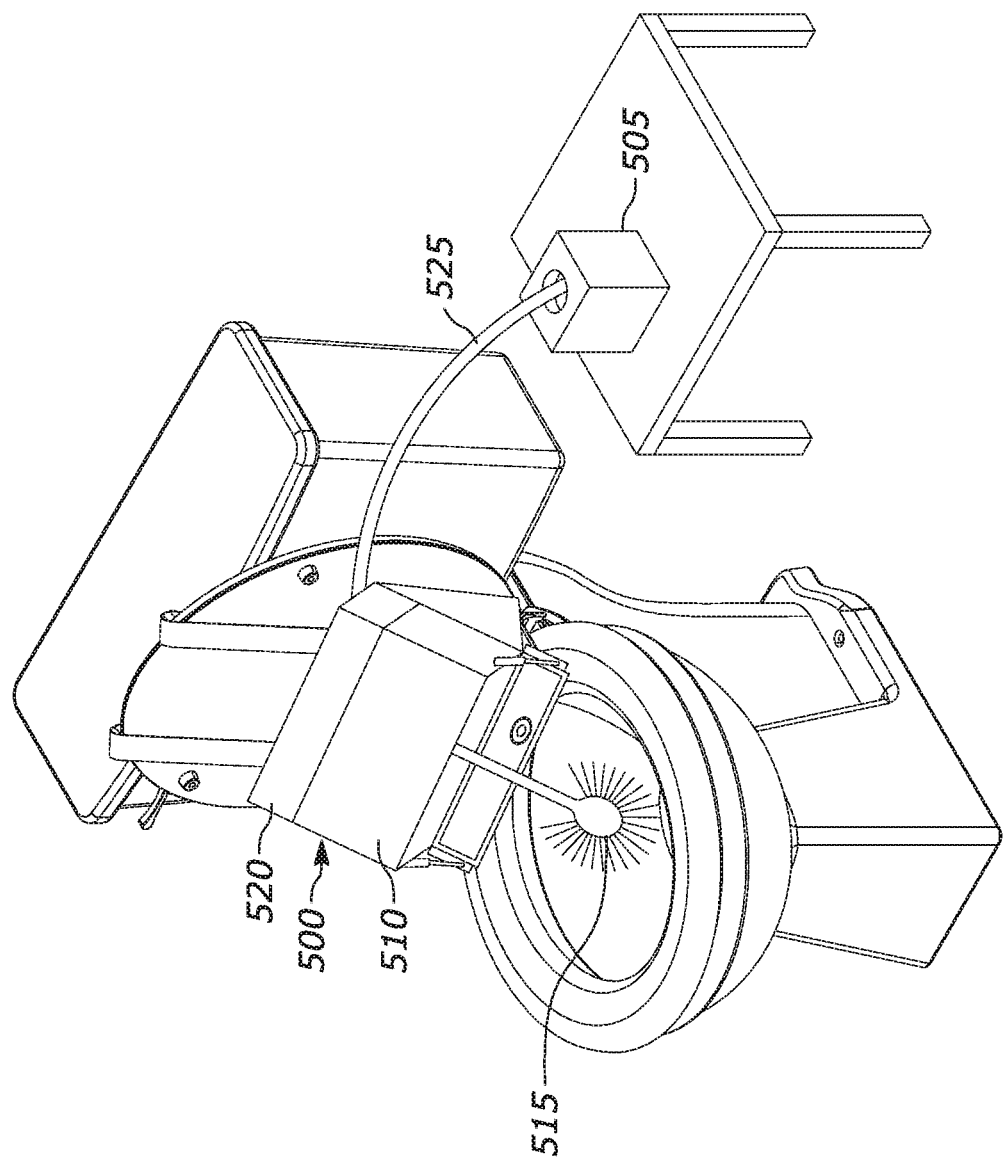
FIG. 5 depicts a stool collection device with an external packaging unit in accordance with an illustrative embodiment.

FIG. 5 depicts a stool collection device 500 with an external collection receptacle 505 in accordance with an illustrative embodiment. The stool collection device 500 includes a homogenization chamber 510 with a retractable catchment unit 515 extending therefrom. The stool collection device 500 also includes a solution chamber 520 mounted behind the homogenization chamber 510. The solution chamber 520 can include the homogenizing solution and/or cleaning solution. The external collection receptacle is part of a packaging unit used to collect and package the homogenized stool sample, which is received from the main assembly via a hose 525. The stool collection device 500 can include components similar to and can function similar to the stool collection devices described with reference to FIGS. 1 and 2.

Figure 6:
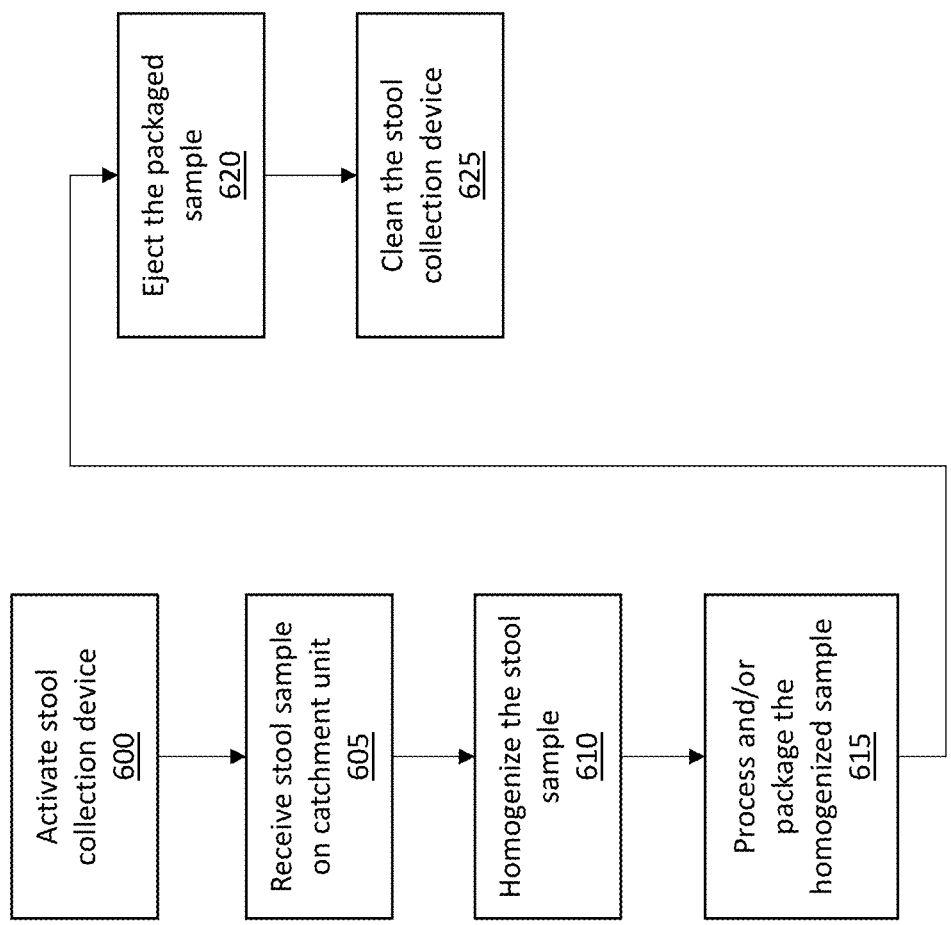
FIG. 6 is a flow diagram depicting operations performed by a stool collection device in accordance with an illustrative embodiment.

FIG. 6 is a flow diagram depicting operations performed by a stool collection device in accordance with an illustrative embodiment. In alternative embodiments, fewer, additional, and/or different operations may be performed. Also, the use of a flow diagram is not meant to limiting with respect to the order of operations performed. In an operation 600, the stool collection device is activated. The stool collection device can be activated in response to an activation instruction received from a user. The instruction can be received as a result of pressing a button or activating a switch. The instruction can also be a wireless signal received from a user device such as a smart phone, tablet, laptop, etc. The instruction can also be responsive to the detection of motion on or near the toilet by a motion sensor. Activation of the stool collection device includes positioning of a catchment unit to collect a stool sample within a toilet. In an alternative embodiment, the stool collection device may automatically revert to a 'ready' position after a prior stool sample is received/processed/packaged so that no user action is involved in the activation process.

In an operation 605, the stool collection device receives a stool sample on the catchment unit. Upon receipt of the stool sample, the catchment unit (with sample thereon) is retracted within a homogenization chamber using any of the techniques described herein. In an operation 610, the stool sample is homogenized. In an illustrative embodiment, a homogenizing solution is brought into the homogenization chamber along with the stool sample. The stool sample is removed from the catchment unit and placed into the homogenizing solution via agitation of the catchment unit and/or forced movement of the homogenizing solution.

In an operation 615, the homogenized stool sample is processed and/or packaged at the stool collection device. In an embodiment in which the stool sample is processed, the homogenized stool sample can be heated, analyzed, and tested using any techniques known in the art. Results of the analysis can be stored in a memory of the stool collection device and/or transmitted to a remote location for review and further analysis. Packaging of the homogenized stool sample involves placement of the stool sample in a container and sealing the container. In an operation 620, the packaged stool sample is ejected from the stool collection device. Ejection can involve opening of a door or panel that allows the user to access the container into which the stool sample has been placed. A user is then able to access the (clean) container and send the homogenized stool sample to a laboratory for processing. In an alternative embodiment with an external packaging unit such as that depicted in FIG. 5, the packaged stool sample is already accessible to the user and does not need to be ejected from the device.

In an operation 625, the stool collection device is cleaned. Cleaning the stool collection device involves soaking and flushing all components of the device that contacted the stool sample with a cleaning solution such as bleach or another disinfectant. Any of the cleaning techniques described herein may be used. Once the stool collection device is clean, the process reverts back to the operation 600 in which the stool collection device either automatically activates and awaits another stool sample or waits for an activation instruction from a user of the device.

In an illustrative embodiment, the methods described herein may be performed at least in part by a computing device. In addition, any of the operations described herein may be implemented as computer-readable instructions stored on a tangible computer-readable medium such as a memory. Upon execution of the computer-readable instructions by a processor, the operations described herein are carried out.

Figure 7:
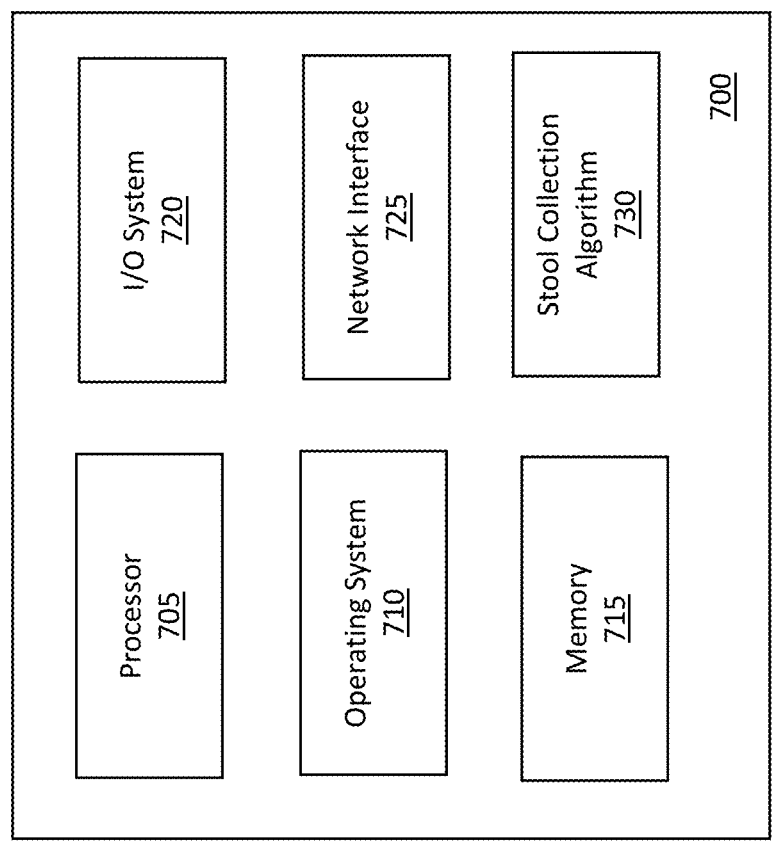
FIG. 7 is a block of a computing system for a stool collection device in accordance with an illustrative embodiment.

FIG. 7 is a block diagram of a computing system 700 for a stool collection device in accordance with an illustrative embodiment. The computing system 700 includes a processor 705, an operating system 710, a memory 715, an input/output (I/O) system 720, a network interface 725, and a stool collection algorithm 730. In alternative embodiments, the computing system 700 may include fewer, additional, and/or different components. The components of the computing system communicate with one another via one or more buses, one or more wires, a wireless communication protocol, or any other interconnect system. The computing system 700 can be incorporated into any portion(s) of the stool collection devices described herein. In an alternative embodiment, one or more components of the computing system 700 can also be incorporated into a remote device such as a laptop computer, desktop computer, smart phone, tablet, workstation, server, etc.

The processor 705 can be any type of computer processor known in the art, and can include a plurality of processors and/or a plurality of processing cores. The processor 705 can include a controller, a microcontroller, sensor processor(s), a hardware accelerator, a digital signal processor, etc. Additionally, the processor 705 may be implemented as a complex instruction set computer processor, a reduced instruction set computer processor, an x86 instruction set computer processor, etc. The processor is used to run the operating system 710, which can be any type of operating system. The processor 705 uses the stool collection algorithm 730 to perform any of the stool collections described herein, such as device activation, catchment unit control, homogenization, cleaning, sample processing, sample packaging, fluid pumping, motor control, solenoid control, etc.

The operating system 710 is stored in the memory 715, which is also used to store programs, user and/or stool sample data, network and communications data, peripheral component data, and the stool collection algorithm 730. The memory 715 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 720 is the framework which enables users and peripheral devices to interact with the computing system 700. The I/O system 720 can include any user interfaces that allow the user to interact with and control the computing system 700, such as control buttons/switches, a display, etc. The I/O system 720 also includes circuitry and a bus structure to interface with peripheral computing devices such as power sources, USB devices, peripheral component interconnect express (PCIe) devices, serial advanced technology attachment (SATA) devices, proprietary connection devices, etc.

The network interface 725 includes transceiver circuitry that allows the computing system to transmit and receive data to/from other devices such as remote computing systems, servers, websites, etc. The network interface 725 enables communication through a network (not shown), which can be one or more communication networks. The network can include a cable network, a fiber network, a cellular network, a wi-fi network, a landline telephone network, a microwave network, a satellite network, etc. The network interface 725 also includes circuitry to allow device-to-device communication such as Bluetooth® communication. In one embodiment in which sample processing is performed, the network interface 725 is used to transmit results of the sample processing to a remote system for further analysis and consideration. General information regarding the stool sample such as patient name, time of collection, date of collection, etc. can also be stored in the memory 715 and/or transmitted to a remote system using the network interface 725.

The stool collection algorithm 730 can include computer-readable instructions stored in the memory 715 that, upon execution, perform any of the stool sample collection operations described herein. The stool collection algorithm 730 can be programmed and compiled using any techniques known in the art. In an alternative embodiment, the stool collection algorithm 730 can be remote or independent from the rest of the computing system 700, but in communication therewith.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A stool sample collection device comprising:
    a catchment unit positioned within a toilet bowl and configured to receive a stool sample;
    a homogenization chamber in which the stool sample is homogenized in a homogenizing solution, wherein the homogenization chamber is configured to receive the stool sample from the catchment unit; and
    a motor configured to retract the catchment unit within the homogenization chamber after the stool sample is received thereon, wherein the motor is configured to agitate the catchment unit to assist in removing the stool sample from the catchment unit during homogenization.

2. The stool sample collection device of claim 1, further comprising a homogenizing solution chamber configured to store the homogenizing solution.

3. The stool sample collection device of claim 2, further comprising a pump configured to move the homogenizing solution from the homogenizing solution chamber to the homogenization chamber.

4. The stool sample collection device of claim 1, wherein the catchment unit includes a catch arm and a plurality of catch fingers mounted to the catch arm.

5. The stool sample collection device of claim 1, further comprising a cleaning solution chamber configured to store a cleaning solution for use in cleaning portions of the stool collection device that are in contact with the stool sample.

6. The stool sample collection device of claim 1, further comprising an analysis unit that is configured to receive and analyze the homogenized stool sample.

7. The stool sample collection device of claim 1, further comprising a packaging unit that is configured to receive and package the homogenized stool sample.

8. A method of collecting a stool sample comprising:
    receiving a stool sample on a catchment unit of a stool sample collection device;
    retracting the catchment unit and the stool sample into a homogenization chamber of the stool sample collection device;

homogenizing the stool sample with a homogenizing solution within the homogenization chamber;

retracting, by a motor, the catchment unit within the homogenization chamber after the stool sample is received thereon; and agitating, by the motor, the catchment unit to assist in removing the stool sample from the catchment unit during homogenization.

9. The method of claim 8, further comprising cleaning the stool sample collection device with a cleaning solution.

10. The method of claim 9, wherein cleaning the stool sample collection device includes flushing the homogenization chamber and the catchment unit with the cleaning solution.

11. The method of claim 8, further comprising pumping the homogenizing solution from a homogenizing solution chamber into the homogenization chamber.

12. The method of claim 8, further comprising:

providing the homogenized stool sample to an analysis unit; and analyzing the sample with the analysis unit.

13. The method of claim 8, further comprising packaging the homogenized stool sample with a packaging unit.

14. A stool sample collection device comprising:

a catchment unit positioned within a toilet bowl and configured to receive a stool sample;

a homogenization chamber, wherein the homogenization chamber includes a door that is in an open position when the catchment unit is extended and a closed position when the catchment unit is retracted within the homogenization chamber; and a processor configured to control the catchment unit and the homogenization chamber, wherein the processor is configured to:

move at least a portion of the catchment unit that includes the stool sample into the homogenization chamber;

homogenize the stool sample in a homogenizing solution within the homogenization chamber; and remove the homogenized stool sample from the homogenization chamber.

15. The stool sample collection device of claim 14, wherein the processor is further configured to place at least a portion of the homogenized stool sample into a removable container.

16. The stool sample collection device of claim 14, wherein the processor is further configured to analyze the homogenized stool sample to obtain stool sample data, and further comprising a transceiver operatively coupled to the processor, wherein the transceiver is configured to transmit the stool sample data to a remote location.

\* \* \* \* \*